(12) United States Patent
Scialdone et al.

(10) Patent No.: US 9,072,999 B2
(45) Date of Patent: Jul. 7, 2015

(54) AROMATIC AMINO COMPOUNDS FOR CARBON DIOXIDE AND SULFUR DIOXIDE REMOVAL

(75) Inventors: Mark A. Scialdone, West Grove, PA (US); James A. Schultz, Swedesboro, NJ (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 411 days.

(21) Appl. No.: 13/045,674

(22) Filed: Mar. 11, 2011

(65) Prior Publication Data

US 2011/0223086 A1 Sep. 15, 2011

Related U.S. Application Data

(60) Provisional application No. 61/313,312, filed on Mar. 12, 2010.

(51) Int. Cl.
| | |
|---|---|
| *B01D 53/46* | (2006.01) |
| *B01D 53/50* | (2006.01) |
| *B01D 53/62* | (2006.01) |
| *B01D 53/14* | (2006.01) |
| *B01D 53/74* | (2006.01) |
| *B01D 53/96* | (2006.01) |
| *B01D 53/02* | (2006.01) |
| *B01D 53/22* | (2006.01) |
| *B01D 61/38* | (2006.01) |
| *C07C 209/90* | (2006.01) |

(52) U.S. Cl.
CPC ............ *B01D 53/02* (2013.01); *B01D 53/1475* (2013.01); *B01D 53/1481* (2013.01); *B01D 53/1493* (2013.01); *B01D 53/228* (2013.01); *B01D 53/507* (2013.01); *B01D 53/62* (2013.01); *B01D 61/38* (2013.01); *B01D 2252/2041* (2013.01); *B01D 2252/20436* (2013.01); *C07C 209/90* (2013.01); *Y02C 10/04* (2013.01)

(58) Field of Classification Search
USPC ................. 423/220, 228, 242.1, 242.2, 242.7
See application file for complete search history.

(56) References Cited

U.S. PATENT DOCUMENTS

| T970,008 | I4 * | 5/1978 | Kohler et al. ............... 423/242.7 |
|---|---|---|---|
| 4,139,597 | A * | 2/1979 | Kohler et al. ............... 423/242.7 |
| 4,208,387 | A | 6/1980 | Klass |
| 4,845,218 | A | 7/1989 | Schroeder |
| 4,917,873 | A | 4/1990 | Filss |
| 5,077,023 | A * | 12/1991 | Leutner et al. ............. 423/242.4 |
| 6,579,343 | B2 | 6/2003 | Brennecke et al. |
| 7,214,358 | B2 | 5/2007 | Ravary |
| 2005/0129598 | A1 | 6/2005 | Chinn et al. |
| 2007/0264180 | A1 | 11/2007 | Carrette |
| 2008/0236390 | A1 | 10/2008 | Anders et al. |
| 2011/0220506 | A1 | 9/2011 | Kelkar |
| 2011/0223084 | A1 | 9/2011 | Scialdone |
| 2011/0223085 | A1 | 9/2011 | Kelkar |
| 2011/0223087 | A1 | 9/2011 | Lustig |
| 2011/0223093 | A1 | 9/2011 | Scialdone |
| 2011/0224427 | A1 | 9/2011 | Scialdone |
| 2011/0296992 | A1 | 12/2011 | Scialdone |
| 2011/0296993 | A1 | 12/2011 | Foo |
| 2013/0269526 | A1 | 10/2013 | Lustig |

FOREIGN PATENT DOCUMENTS

| WO | WO 2006/000845 | * | 1/2006 | ............ C07C 269/04 |
|---|---|---|---|---|
| WO | 2008/122030 A1 | | 10/2008 | |
| WO | WO2009/061470 | * | 5/2009 | ............... B01J 20/30 |
| WO | 2010/010238 A1 | | 1/2010 | |
| WO | 2010/010239 A1 | | 1/2010 | |

OTHER PUBLICATIONS

Silver, F.M., "Aromatic Polyamides. IV. A Novel Synthesis of Sulfonated Poly(para-Phenyleneterephthalamide): Polymerization of Terephthalic Acid and para-Phenylenediamine in Sulfur Trioxide." J. Polymer Sci.: Polymer Chemistry Ed. (Wiley), vol. 17, Issue 11, pp. 3519-3533 (1979).*
Roberts et al., "Basic Principles of Organic Chemistry." W.A. Benjamin, Inc. (c) 1977. (excerpt).*
Roberts et al., "Basic Principles of Organic Chemistry." W.A. Benjamin, Inc. (c) 1977. (excerpt: pp. 1095, 1157).*
Acros Organics, "2000/01 Catalog of Organics." (c) 2001 Fisher Scientific Co. L.L.C. (excerpt).*
Bates et al, "$CO_2$ Capture by a Task-Specific Ionic Liquid", Journal of the American Chemical Society, vol. 124, No. 6, 2002, pp. 926-927.
Gutowski et al, "Amine-Functionalized Task-Specific Ionic Liquids: A Mechanistic Explanation for the Dramatic Increase in Viscosity Upon Complexation With $CO_2$ From Molecular Simulation", Journal of American Chemical Society, 130: 14690-14704 (2008).
Mark A. Scialdone, U.S. Appl. No. 13/045,820, filed Mar. 11, 2011.
Mark A. Scialdone, U.S. Appl. No. 13/046,009, filed Mar. 11, 2011.
Mark A. Scialdone, U.S. Appl. No. 13/044,902, filed Mar. 10, 2011.
Steven Raymond Lustig, U.S. Appl. No. 13/045,911, filed Mar. 11, 2011.
Manish S. Kelkar, U.S. Appl. No. 13/045,617, filed Mar. 11, 2011.

* cited by examiner

*Primary Examiner* — Stanley Silverman
*Assistant Examiner* — Daniel Berns

(57) ABSTRACT

Described are aromatic amino compounds that are useful to methods of carbon dioxide and sulfur dioxide removal.

17 Claims, No Drawings

AROMATIC AMINO COMPOUNDS FOR CARBON DIOXIDE AND SULFUR DIOXIDE REMOVAL

This application claims priority under 35 U.S.C. §119(e) from, and claims the benefit of, U.S. Provisional Application No. 61/313,312, filed Mar. 12, 2010, which is by this reference incorporated in its entirety as a part hereof for all purposes.

TECHNICAL FIELD

This invention relates to amino compounds that are useful to methods of carbon dioxide and sulfur dioxide capture and removal.

BACKGROUND

There is increasing interest in methods to reduce or capture $CO_2$ from many different gaseous mixtures. $CO_2$ is an undesired component that is present in many gas streams such as natural gas and effluent gases, and there is also much global interest in reducing $CO_2$ emissions from combustion exhaust for the prevention of global warming. $CO_2$ can be removed or captured by many means, such as physical or chemical absorption of the gas by a liquid or solid.

Currently, a common method of carbon dioxide capture from process streams in industrial complexes involves the use of aqueous solutions of alkanolamines, but usually on a small scale. The process has been used commercially since the early 1930s (see, for example, Kohl and Nielsen, Gas Purification, 5th Edition, Gulf Publishing, Houston Tex., 1997), and is based on the reaction of a weak base (alkanolamine) with a weak acid ($CO_2$) to produce a water-soluble salt. This reaction is reversible, and the equilibrium is temperature dependent.

The use of alkanolamines as absorbents for $CO_2$ (from power plant flue gases, for example) is somewhat disadvantaged in respect of the amount of energy needed to regenerate the $CO_2$-rich solvent, the size of the $CO_2$ capture plant, and the loss of alkanolamines to the environment. Among conventional alkanolamines, monoethanolamine (MEA) is considered an attractive solvent at low partial pressures of $CO_2$ because it reacts at a rapid rate and the cost of the raw materials is low compared to that of secondary and tertiary amines. The costs of absorption processes using MEA are high, however, because of the high energy consumption in regeneration, and because of operation problems such as corrosion, solvent loss and solvent degradation. Furthermore, MEA can be loaded up to only 0.5 mol of $CO_2$/mol of MEA, or 33 mol %, as a result of the stable carbonates formed.

Physical absorption systems have advantages over chemical absorption such as lower energy costs, but also have disadvantages such as solvent losses and low $CO_2$ capacity. A need thus remains for systems and materials capable of providing low-cost, high-capacity methods of $CO_2$ capture.

SUMMARY

This invention provides a method for the removal of $CO_2$ and/or $SO_2$ from a gaseous mixture by contacting the gaseous mixture with one or more compounds represented by the structure of the following Formula I, or salts thereof:

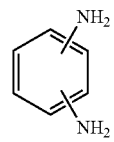

DETAILED DESCRIPTION

There are provided methods for removal of $CO_2$ and/or $SO_2$ from a gaseous mixture in which it is contained comprising contacting the gaseous mixture with one or more compounds represented by the structure of the Formula I, or the salts thereof:

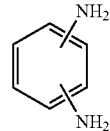

Formula I

The method optionally involves an additional step of recovering a reaction product (such as a compound or an adduct) formed between $CO_2$ and/or $SO_2$ and a Formula I compound; and also involves yet another optional step of separating $CO_2$ and/or $SO_2$ from the Formula I compound, and recovering either or both of $CO_2$ and/or $SO_2$ and the Formula I compound. Separation can be effected by heating or the use of a non-solvent.

The amino groups can be located at any position on the ring. In separate embodiments, the invention thus includes the use of ortho-phenylene diamine, meta-phenylene diamine and para-phenylene diamine. Formula I compounds can be prepared from hydrogenation of the corresponding dinitroaromatic compounds, and the precursor dinitro-aromatic compounds are obtained from nitration of aromatic compounds such as benzene. For example, a nitroaromatic compound can be hydrogenated in the presence of a catalyst containing 0.01-5 wt % of an active component such as Ni, Pd and one other metal such as Co or Fe supported on an activated carbon, carbon black, graphite or metal oxides. Such a catalyst can contain. 0.80 wt % Pd, 13 wt % Ni and 0.93 wt % Sn supported on an activated carbon (such as Norit SX+). Toluenediamine can thus be obtained by hydrogenating dinitrotoluene in a 300 mL reactor at 130° C. and at $H_2$ pressure 25 bar with a selectivity of 98.47%, Methods similar to these are further described in sources such as US 2010/0130788, which is by this reference incorporated as a part hereof for all purposes.

In another embodiment, the compounds of Formula I forms a salt with HX, where HX is an acid with an acidic proton that forms a monofunctionalized salt of the parent diamine. The acid may be a mineral acid or a carboxylic acid. The acid may, for example, consist of, but is not limited to, HCl, $H_2SO_4$, $H_3PO_4$, $HNO_3$, or any other acid capable of donating a proton to the parent amine. Other acids suitable for use for this purpose include acetic acid, formic acid and oxalic acid.

Without wishing to be bound by theory, for the structures described herein, it is believed that the carbon dioxide reacts with the protonated amine to form a carbamate in a more readily reversibly reaction than with the unprotonated parent amine. Therefore, the $CO_2$ and/or $SO_2$ binding will be reversible under milder conditions than with the parent amine.

These milder conditions may be a smaller increase in temperature, a smaller reduction in the partial pressure of $CO_2$ and/or $SO_2$ or a smaller change in pH.

The compounds described herein are thus useful for separation methods such as $CO_2$ and/or $SO_2$ absorption, adsorption, or other types of recovery. This can be accomplished by contacting a gaseous mixture containing $CO_2$ and/or $SO_2$ with one or more of the compounds represented by the structures of Formula I, as defined above. The Formula I compound(s) may be used without dilution or with dilution as an aqueous or other solution. The gaseous mixture containing $CO_2$ and/or $SO_2$ can be any mixture of which $CO_2$ and/or $SO_2$ is a constituent part, or can be 100% $CO_2$ and/or $SO_2$. Examples of gaseous mixtures containing $CO_2$ and/or $SO_2$ include without limitation flue gases, combustion exhausts, natural gas streams, streams from rebreathing apparatus, and the products of chemical synthesis, degradation or fermentation operations. The gases and gaseous mixtures referred to herein may include vapors (volatilized liquids), gaseous compounds and/or other gaseous elements.

Contacting the compounds of Formula I with a gaseous mixture containing $CO_2$ and/or $SO_2$ may be accomplished by any means that promotes intimate mixing of the compounds with the source gas and is conducted for a time sufficient to allow significant removal of the targeted component(s). Thus, systems maximizing surface area contact are desirable. The conditions at which the process are conducted vary according to the compounds of the gaseous stream, the partial pressure of the $CO_2$, and/or $SO_2$ and equipment used, but in suitable embodiments be at temperatures ranging from ambient to about 200° C., and at pressures ranging from 1-5 atmospheres.

Illustratively, contacting the compounds of Formula I with a gaseous mixture can be performed by use of conventional liquid absorbers, such as counter-current liquid absorbers or cyclone scrubbers, by permeation through a supported liquid membrane, or by use of a fixed bed.

In one embodiment hereof, a liquid solvent can be used to remove a compound from a gas stream in an absorber, where gas and liquid are brought into contact countercurrently, and the gas is dissolved into the solvent. The absorber is typically equipped with trays or packing to provide a large liquid-gas contact area. Valve and sieve trays may be used, as may bubble cap and tunnel trays, where a tray typically has overflow weirs and downcomers to create hydrostatic holdup of the downward flow of the liquid. Random packings can also be used such as Rashig rings, Pall rings or Berl saddles, or structured packings of woven or nonwoven fabrics of metal, synthetic materials or ceramics.

The purified gas is taken off the head of the column. The solvent laden with the absorbed compound is withdrawn from the bottom of the absorber, routed to a regeneration system where it is freed of absorbed the absorbed gas component, and returned as lean solvent to the absorber. Regeneration may be accomplished by flash regeneration, which can involve pressure reduction and mild reboiling in one or more stages; by inert gas stripping; or by high temperature reboiling wherein the solvent is stripped by its own vapor, which is then condensed from the overhead gas and recycled as reflux.

In an absorber, a batch process may be performed where the flow rate through the vessel correlates to the residence time of contact and is suitably chosen to afford an effluent stream with the desired purification tolerance. To promote the desired intimate mixing, such gas/liquid absorption units also may be operated in a dual flow mode. Such dual flow can be co-current or counter-current. In such an embodiment, the gas mixture and the compounds of Formula I flow through a purification unit contemporaneously. Methods for carbon dioxide absorption are further discussed in U.S. Pat. No. 6,579,343; US 2005/0129598; and US 2008/0236390 (each of which is by this reference incorporated as a part hereof for all purposes).

Where supported liquid membranes are used for gas recovery, the membrane may include a solvent such as the compounds of Formula I contained within the pores of a solid microporous support, such as a ceramic, metal, or polymeric support. Supported liquid membranes fabricated from supports such as ceramics, metals, and certain heat stable polymers may advantageously be used in higher than ambient temperature operations. Such higher temperature operations may be preferred to effect a more rapid separation, requiring less contact time. In addition, these higher temperature operations may also be a consequence of the process configuration, such as configurations requiring purification of high temperature exhaust gases or other gases exiting high temperature operations. Supported liquid membranes suitable for purifying high temperature gases obviate the need to pre-cool such gases before contact with the supported liquid membrane. The supported liquid membranes may be fabricated as thin films or hollow fibers with continuous networks of interconnected pores leading from one surface to the other. Supported liquid membranes contact a feed gas mixture on one side of the membrane and may effect separation of a gas component from the mixture by allowing that component to escape via permeation or diffusion into the compounds of Formula I and through the liquid membrane.

The compounds of Formula I can also be used in a conventional gas/liquid absorption unit-based system comprising a fixed bed. Such systems can be operated in batch mode or continuous flow mode. In a typical batch mode configuration, the compounds of Formula I are introduced into a vessel followed by introduction of the gas mixture. After a prescribed residence time, the resulting gas is removed, leaving behind an impurity or group of impurities dissolved in the compounds of Formula I or Formula II. The batch purified gas can be generated by heating or reduced pressure treatment as described above. To maximize contact of the compound and the gas mixture, the compounds of Formula I can be coated on a solid support, such as glass beads, and the like, to increase the surface area capable of contacting the gas mixture.

In one embodiment, this invention provides a method wherein the removal of $CO_2$ and/or $SO_2$ from a gaseous mixture occurs in a removal apparatus; wherein, in the removal apparatus, $CO_2$ and/or $SO_2$ is dissolved into a Formula (I) compound(s) to form (i) a purified fraction that is depleted in $CO_2$ and/or $SO_2$ content (compared to the content thereof in the original feed of the gaseous mixture) and (ii) a solvent fraction that is enriched in $CO_2$ and/or $SO_2$ content (compared to the content thereof in the original feed of the gaseous mixture); and wherein the solvent fraction is separated from the removal apparatus. In a further alternative embodiment of the methods hereof, $CO_2$ and/or $SO_2$ can be separated from the solvent fraction to form a rectified solvent fraction, and the rectified solvent fraction can be returned to the removal apparatus.

Equipment and processes that can be used for the absorption of $CO_2$ and/or $SO_2$ are further described in Absorption, Ullmann's Encyclopedia of Industrial Chemistry [2002, (Wiley-VCH Verlag GmbH & Co. KGa) Johann Schlauer and Manfred Kriebel, Jun. 15, 2000 (DOI: 10.1002/14356007.b03_08)]; and Absorption, Kirk-Othmer Encyclopedia of Chemical Technology [2003, (John Wiley & Sons, Inc), Manuel Laso and Urs von Stockar (DOL10.1002/0471238961.0102191519201503.a01.pub2)].

Various materials suitable for use herein may be made by processes known in the art, and/or are available commercially from suppliers such as Alfa Aesar (Ward Hill, Mass.), City Chemical (West Haven, Conn.), Fisher Scientific (Fairlawn, N.J.), Sigma-Aldrich (St. Louis, Mo.) or Stanford Materials (Aliso Viejo, Calif.).

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

Other related systems, materials and methods for the removal of $CO_2$ or $SO_2$ from a gaseous mixture are disclosed in the following concurrently-filed U.S. patent applications:

U.S. Prov. App. No. 61/313,298, U.S. Prov. App. No. 61/414,532, and U.S. Prov. App. No. 61/416,421 (together filed as U.S. Ser. No. 13/045,911, together published as US 2011/0 223 087);

U.S. Prov. App. No. 61/313,173 (U.S. Ser. No. 13/045,578, published as US 2011/0 224 427);

U.S. Prov. App. No. 61/313,181 (U.S. Ser. No. 13/045,820, published as US 2011/0 223 093);

U.S. Prov. App. No. 61/313,322 (U.S. Ser. No. 13/044,782, published as US 2011/0 223 085);

U.S. Prov. App. No. 61/313,328 (U.S. Ser. No. 13/045,617, published as US 2011/0 220 506);

U.S. Prov. App. No. 61/313,312 (U.S. Ser. No. 13/045,674, published as US 2011/0 223 086);

U.S. Prov. App. No. 61/313,183 (U.S. Ser. No. 13/046,009 published as US 2011/0 296 992); and U.S. Prov. App. No. 61/313,191 (U.S. Ser. No. 13/044,902, published as US 2011/0 223 084);

each of which is by this reference incorporated in its entirety as a part hereof for all purposes.

What is claimed is:

1. A method for the removal of $CO_2$ and/or $SO_2$ from a gaseous mixture comprising contacting the gaseous mixture with a liquid or solid material comprising one or more compounds represented by the structure of the Formula I:

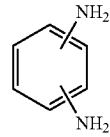

Formula I and removing $CO_2$ and/or $SO_2$ from the mixture;
wherein the Formula I compound is in the form of a salt formed with the acid HX, which acid has an acidic proton;
wherein the removal of one or more of $CO_2$ and/or $SO_2$ from the gaseous mixture occurs in a removal apparatus;
wherein, in the removal apparatus, one or more of $CO_2$ and/or $SO_2$ is dissolved into a compound of Formula I to form (i) a purified fraction that is depleted in one or more of $CO_2$ and/or $SO_2$ content, and (ii) a solvent fraction that is enriched in one or more of $CO_2$ and/or $SO_2$ content; and
wherein the solvent fraction is separated from the removal apparatus.

2. The method of claim 1 wherein one or more of $CO_2$ and/or $SO_2$ is separated from the solvent fraction to form a rectified solvent fraction, and the rectified solvent fraction is returned to the removal apparatus.

3. The method of claim 1 wherein $CO_2$ is removed from the gaseous mixture.

4. The method of claim 1 wherein the Formula I compound comprises ortho-phenylene diamine.

5. The method of claim 1 wherein the Formula I compound comprises meta-phenylene diamine.

6. The method of claim 1 wherein the Formula I compound comprises para-phenylene diamine.

7. The method of claim 1 wherein an acid is selected from the group consisting of a mineral acid and a carboxylic acid.

8. The method of claim 1 wherein $SO_2$ is removed from the gaseous mixture.

9. The method of claim 1 wherein $CO_2$ and/or $SO_2$ is removed from the mixture in a counter-current liquid absorber, in a cyclone scrubber, in a supported liquid membrane, or in a fixed bed.

10. A method for the removal of $CO_2$ and/or $SO_2$ from a gaseous mixture comprising contacting the gaseous mixture with a liquid or solid material without dilution of the liquid or solid material;
wherein the liquid or solid material comprises one or more compounds represented by the structure of the Formula I:

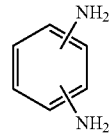

Formula I and removing $CO_2$ and/or $SO_2$ from the gaseous mixture.

11. The method of claim 10 wherein the Formula I compound comprises ortho-phenylene diamine.

12. The method of claim 10 wherein the Formula I compound comprises meta-phenylene diamine.

13. The method of claim 10 wherein the Formula I compound comprises para-phenylene diamine.

14. The method of claim 10 wherein $CO_2$ is removed from the gaseous mixture.

15. The method of claim 10 wherein $SO_2$ is removed from the gaseous mixture.

16. The method of claim 10 wherein $CO_2$ and/or $SO_2$ is removed from the gaseous mixture in a counter current liquid absorber, in a cyclone scrubber, in a supported liquid membrane, or in a fixed bed.

17. The method of claim 10 that further comprises removing $CO_2$ and/or $SO_2$ from the gaseous mixture along with liquid or solid material, and separating $CO_2$ and/or $SO_2$ from the liquid or solid material.

\* \* \* \* \*